United States Patent [19]

Corliss

[11] Plant 5,041

[45] Apr. 19, 1983

[54] JUNIPER PLANT - CORCORCOR VARIETY

[75] Inventor: Clifford D. Corliss, Ipswich, Mass.

[73] Assignee: The Conard-Pyle Company, West Grove, Pa.

[21] Appl. No.: 276,063

[22] Filed: Jun. 22, 1981

[51] Int. Cl.[3] ..... A01H 5/12

[52] U.S. Cl. ..... Plt./50

[58] Field of Search ..... Plt./50

*Primary Examiner*—Robert E. Bagwill

*Attorney, Agent, or Firm*—Burns, Doane, Swecker & Mathis

[57] ABSTRACT

A new and distinct Juniperus variety is provided which originated as a chance seedling from a number of *Juniperus virginiana* seeds planted in a cultivated area at Ipswich, Mass. The new Juniper variety described hereafter is an attractive rapid grower which assumes a dense columnar configuration which renders it well suited for a wide range of landscape requirements.

2 Drawing Figures

SUMMARY OF THE INVENTION

The new variety was discovered and selected by me during 1967 as a chance seedling while present in a cultivated group of young plants of *Juniperus virginiana* being grown under my direction at the nursery property of Corliss Bros., Inc. at Ipswich, Mass. A single plant of the new variety was selected because of its distinctive characteristics.

More specifically, the following combination of characteristics is exhibited by the new Juniperus variety:

(a) an upright evergreen conifer which assumes a columnar configuration which is more dense than the *Juniperus virginiana* parent and substantially similar to that of *Juniperus virginiana Hillii,*

(b) an extremely hardy, vigorous and disease resistant shrub which can be readily sheared within predetermined limits, and which is substantially more vigorous than both *Juniperus virginiana* and *Juniperus virginiana Hillii* and is usually larger than *Juniperus virginiana* and is larger than *Juniperus virginiana Hillii,*

(c) a plant which from a distance is similar in color and shape to the *Juniperus virginiana* parent, but which is much quicker growing and which retains its older foliage for a longer period, giving the new variety a substantially denser appearance, (d) a facility for propagation which represents a marked improvement over the *Juniperus virginiana* parent, thus making the new variety of particular interest to commercial nurserymen, (e) mature (e.g., two year old) foliage which is considerably darker in coloration and slightly glossier than that of the *Juniperus virginiana* parent and when compared to *Juniperus virginiana Hillii* is more emerald green rather than the glaucous green coloration of *Juniperus virginiana Hillii,*

(f) young foliage which is a truer and deeper emerald green than *Juniperus virginiana Hillii* and than the slightly grayed-green foliage commonly exhibited by the *Juniperus virginiana* parent, (g) a much more free-branching character than the *Juniperus virginiana* parent with at least twice the number of shoots on side branches arising from a lateral branch on a main limb than the parent giving the new variety a much denser aspect, and (h) main, lateral and side branches which are perceptively thicker and more robust than those of the *Juniperus virginiana* parent.

Asexual reproduction of my new variety by cuttings has been accomplished at Ipswich, Mass. and West Grove, Pa. Such propagation has demonstrated that the unique combination of characteristics is fully established and is transmitted to successive generations.

The new variety has been named the Corcorcor variety.

BRIEF DESCRIPTION OF THE PHOTOGRAPHS

The accompanying photographs show typical specimens of my new variety of Juniperus as depicted in color as true as is reasonably possible to make the same in color photographs of this character. The specimens in the photographs are six year old plants growing in the landscape during late spring at West Grove, Pa.

FIG. 1 illustrates the attractive dense columnar growth habit of a representative six year old plant of the new variety, and FIG. 2 illustrates a representative branch of the new variety wherein the freely-branched previous and current year's growth are apparent.

DETAILED DESCRIPTION

Figure 1:
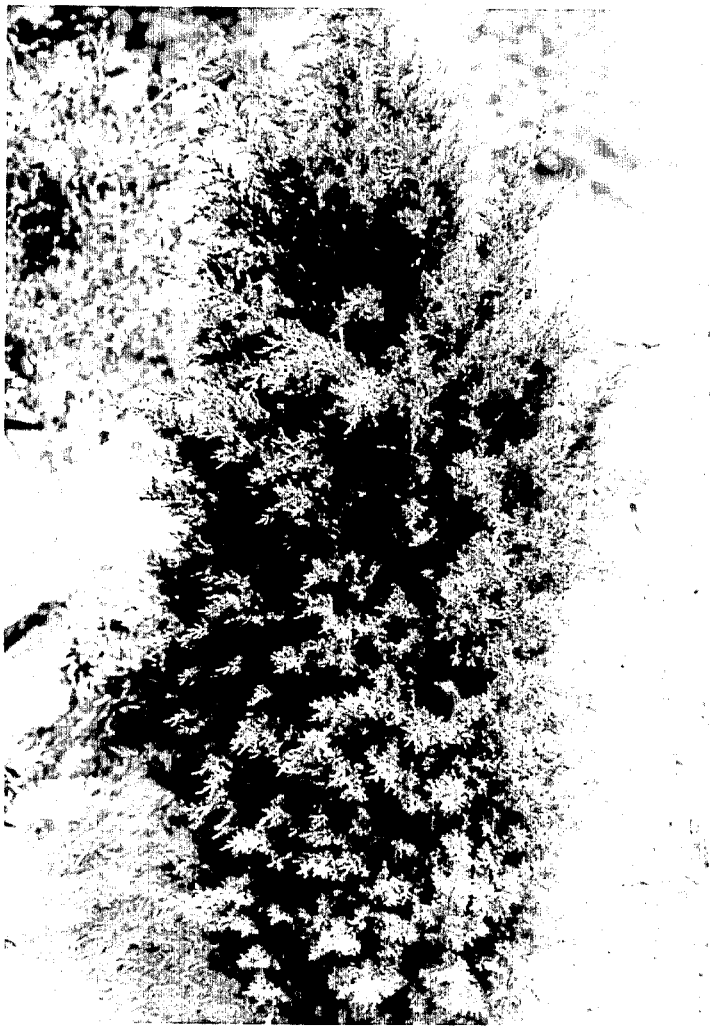
Figure 2:
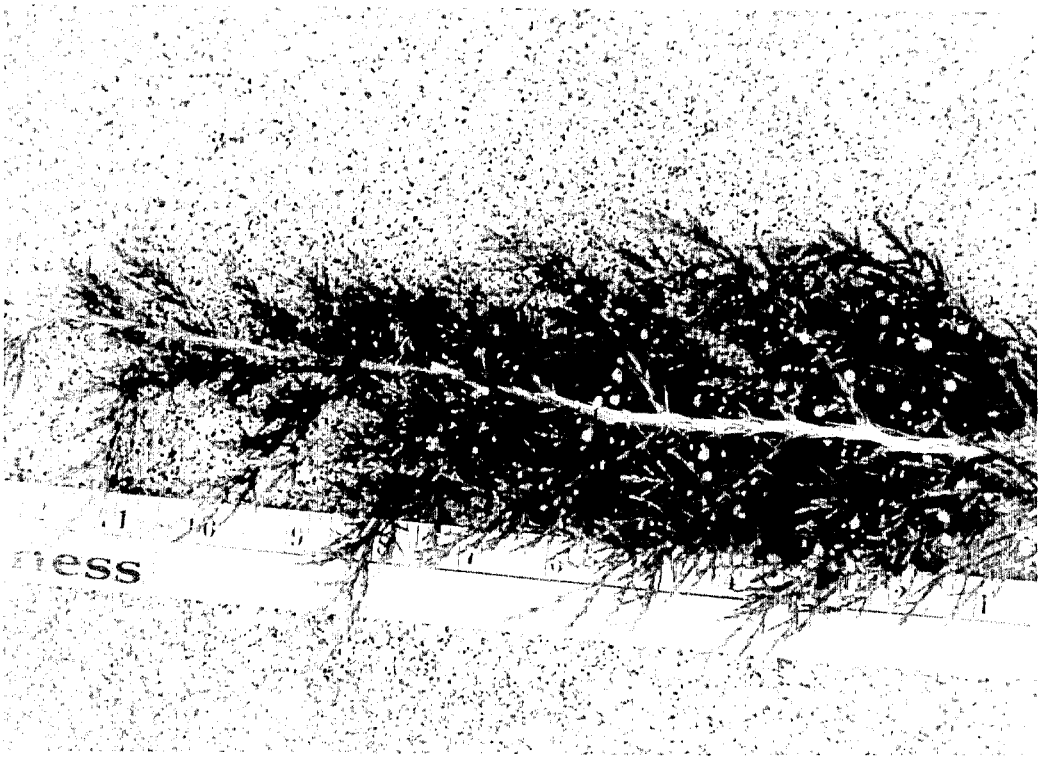

The following is a detailed description of my new variety, with color terminology in accordance with the R.H.S. Colour Chart of The Royal Horticulture Society, London, England. The description was made during late spring following the observation of representative plants which were grown in a landscape setting at West Grove, Pa.

Type: Evergreen conifer.

Growth habit: Symmetrical and conical.

Foliage:

*Type.*—Needle-shaped evergreen. The leaves are typical of those found on *Juniperus virginiana* and *Juniperus virginiana Hillii* with the new growth being prickly and the mature growth more frond-like. However, the foliage is much more free-branching than that of the *Juniperus virginiana* parent giving the plant a more dense configuration as illustrated which is substantially similar to *Juniperus virginiana Hillii.* When compared with the *Juniperus virginiana* parent there are at least twice the number of shoots on side branches arising from a lateral branch on a main limb than the parent.

*Shape.*—Substantially similar to *Juniperus virginiana.*

*Color.*—New growth in late spring — Green Group 143A; growing tip on new growth — Green Group 144A. Previous year's growth in late spring is between Green Group 135A and Green Group 139A. Previous year's growth of dormant plants in late winter — Green Group 135A. During the growing season the emerald green coloration of the new variety is distinct from the glaucous green coloration of *Juniperus virginiana Hillii.* In the winter the plant exhibits a bronzed shade of emerald green which is distinct from the bronzed shade of glaucous green which is exhibited by *Juniperus virginiana Hillii.*

*Internode length on mature main branches.*—Approximately 0.5 cm. to 1.2 cm.

Fruits: Substantially similar to *Juniperus virginiana* in color, shape and size. After reaching an age of approximately six or seven years from the date of asexual propagation plants of the present variety fruit fairly heavily.

Growth rate: Six year old plants growing in the landscape have an average height of approximately 93 inches and average breadth at base of approximately 36 inches. Two year old plants growing in a soilless medium in containers have an average height of approximately 18 to 21 inches and average breadth at the base of approximately 10 to 12 inches. Young plants under four years of age tend to have a very open growth habit which fills in proportionally with the age of the plant. Plants of the present variety exhibit more vigor than the *Juniperus virginiana* parent and than *Juniperus virginiana Hillii* and are usually capable of assuming a larger height than *Juniperus virginiana* and are capable of assuming a larger height than *Juniperus virginiana Hillii* under the same growing conditions.

I claim:

1. A new and distinct variety of Juniperus, substantially as herein shown and described, characterized particularly as to novelty by the unique combination of:

(a) an upright evergreen conifer which assumes a columnar configuration which is more dense than the *Juniperus virginiana* parent and substantially similar to that of *Juniperus virginiana Hillii,*

(b) an extremely hardy, vigorous and disease resistant shrub which can be readily sheared within predetermined limits, and which is substantially more vigorous than both *Juniperus virginiana* and *Juniperus virginiana Hillii* and is usually larger than *Juniperus virginiana* and is larger than *Juniperus virginiana Hillii,*

(c) a plant which from a distance is similar in color and shape to the *Juniperus virginiana* parent, but which is much quicker growing and which retains its older foliage for a longer period, giving the new variety a substantially denser appearance, (d) a facility for propagation which represents a marked improvement over the *Juniperus virginiana* parent, thus making the new variety of particular interest to commercial nurserymen, (e) mature (e.g., two year old) foliage which is considerably darker in coloration and slightly glossier than that of the *Juniperus virginiana* parent and when compared to *Juniperus virginiana Hillii* is more emerald green rather than the glaucous green coloration of *Juniperus virginiana Hillii,*

(f) young foliage which is a truer and deeper emerald green than *Juniperus virginiana Hillii* and than the slightly grayed-green foliage commonly exhibited by the *Juniperus virginiana* parent, (g) a much more free-branching character than the *Juniperus virginiana* parent with at least twice the number of shoots on side branches arising from a lateral branch on a main limb than the parent giving the new variety a much denser aspect, and (h) main, lateral and side branches which are perceptively thicker and more robust than those of the *Juniperus virginiana* parent.

* * * * *